United States Patent [19]

Bloebaum et al.

[11] Patent Number: 4,872,865
[45] Date of Patent: Oct. 10, 1989

[54] HYPERTONIC SOLUTION FOR ARTHROSCOPIC SURGERY

[75] Inventors: Roy D. Bloebaum, Salt Lake City, Utah; Frank P. Magee, Phoenix, Ariz.

[73] Assignee: Harrington Arthritis Research Center, Phoenix, Ariz.

[21] Appl. No.: 125,731

[22] Filed: Nov. 30, 1987

Related U.S. Application Data

[63] Continuation of Ser. No. 785,767, Oct. 9, 1985, abandoned.

[51] Int. Cl.⁴ ............................................. A61M 1/00
[52] U.S. Cl. .......................................... 604/28; 604/49
[58] Field of Search .................................. 604/4–6, 604/49, 50, 51, 52, 53, 28

[56] References Cited

U.S. PATENT DOCUMENTS

| | | | |
|---|---|---|---|
| 3,993,750 | 11/1976 | Fox, Jr. | 424/128 |
| 4,217,891 | 8/1980 | Carson | 128/6 |
| 4,238,482 | 12/1980 | Peyman et al. | 424/180 |
| 4,308,255 | 12/1981 | Raj et al. | 424/156 |
| 4,369,768 | 1/1983 | Vukovic | 128/6 |
| 4,386,072 | 5/1983 | Horrobin et al. | 424/127 |
| 4,443,432 | 4/1984 | Garabedian et al. | 424/127 |
| 4,451,454 | 5/1984 | Wong | 424/127 |
| 4,504,493 | 2/1985 | Marshall et al. | |
| 4,550,022 | 10/1985 | Garabedian et al. | 424/127 |
| 4,608,044 | 8/1986 | Nordqvist et al. | 128/156 |

FOREIGN PATENT DOCUMENTS

0024706  3/1981  European Pat. Off. ............... 128/6

OTHER PUBLICATIONS

AMA Drug Evaluations, Fifth Ed., Chicago, Ill., 1983.
*AMA Drug Evaluations*, 5th Ed., © 1983, American Medical Association, Chicago, Ill., pp. 1108–1120.
Osol ed. Remington's Pharmaceutical Sciences, 16th Ed., Mack Publishing; Easton, Pa., 1980, pp. 761–763.
Feedback Control of Intracranial Pressure Using Mannitol, D. J. Larnard and A. J. Kiovo, Annals of Biomedical Engineering, vol. 11, pp. 227–235, (1985).
Irrigation Solutions for Arthroscopy, B. F. Reagan et al., (1983).
The Effect of Arthroscopic Irrigating Solutions on Cartilage and Synovium, D. Straehley et al., 31st Annual ORS, Las Vegas, Nev., 1985.
Normal Human Synovial Fluid: Osmolality and Exercise-Induced Changes, M. Baumgarten, M.D. et al., The Journal of Bone and Joint Surgery, pp. 1136–1339, (1985).
Hypothermic Subarachnoid Irrigation for Intractable Pain, The Lancet, May 1967, pp. 1133–1135.
A New Isotonic Irrigating Solution for Use in Transurethral Surgery, The Journal of Urology, vol. 100, pp. 88–89.
Hyperiactatemia During Transurethral Resection of the Prostate Using Sorbitol Solution as the Urologic Irrigant, Anesthesiology, 52:374–375, 1980.

*Primary Examiner*—C. Fred Rosenbaum
*Assistant Examiner*—Mark F. Colosimo
*Attorney, Agent, or Firm*—Irell & Manella

[57] ABSTRACT

A physiologically conforming solution for use in invasive medical procedures which is hypertonic with respect to blood serum and may, in fact, have a higher osmolality than synovial fluid. The solution is of particular utility as an irrigant in arthroscopic surgery in order to reduce the risk of swelling and injury of the synovial tissues and as a therapeutic treatment for swelling and subsequent inflammation of joints and soft tissue which occurs in certain traumatized and pathological states.

9 Claims, 5 Drawing Sheets

HYPERTONIC SOLUTION FOR ARTHROSCOPIC SURGERY

The is a continuation of application Ser. No. 785,767 filed Oct. 9, 1985 which was abandoned upon the filing hereof.

BACKGROUND OF THE INVENTION

This invention relates generally to solutions for use in invasive medical procedures and, more specifically, to a hypertonic solution for use in surgical procedures and other therapeutic treatments of the joints and soft tissues.

In recent years, arthroscopic procedures, whereby an arthroscope is used to visually examine the interior of a joint, have become increasingly routine. In addition to its use in diagnostic techniques, arthroscopy has dramatically changed joint surgery. Rather than requiring the complete opening of, for example, the knee, such surgery requires an incision only large enough to permit access of the arthroscope and a mechanized cutting tool. Arthroscopic procedures are now routinely used for many diagnostic and surgical procedures including partial meniscectomy, abrasion arthroplasty and cruciate ligament repair.

One of the clinical complications of arthroscopic procedures is synovitis, or inflammation of the synovial tissues, which can be painful and delay rehabilitation. Post-operative synovitis of the knee, for example, is particularly prevalent after relatively long procedures. During arthroscopic surgery, the tissue must be continuously bathed with an irrigation solution in order to maintain the cavity in a distended condition and wash away any debris resulting from the procedure. Various solutions have been used for such purposes, including sterile water, sterile saline solution, lactated Ringer's, aqueous sugar solutions and glycine solutions. Generally, it has been considered desirable to have the solutions duplicate physiological fluids as closely as possible, and thus attempts have been made to conform, for example, the pH, ionic strength and osmotic pressure to those of blood serum, which has been assumed to represent the standard for all body fluids.

Presently, the standard practice in arthroscopic surgery is to use isotonic irrigants, i.e. those having the molar concentration of electrolytes and osmolality approximately equal to that of blood serum.

Post-operative synovitis may result from chemical irritation of the tissues by the irrigation solution. Sterile saline commonly used in arthroscopic procedures is known to be highly irritating, causing severe synovitis and attendant pain, swelling and stiffness of the joint. Further, microsurgeons working with small, delicate operating microscopes and instrumentation are often hampered by swelling of soft tissues which may result from the irrigant.

Synovial fluid is a mucinous-viscous lubricant surrounding the articular cartilage, ligaments, tendons and nerve structures, in joints such as the knee or the elbow. It is secreted by the synovium and functions to lubricate the articulation and provide nutrition to the cartilage cells. Until recently, it has been generally assumed that synovial fluid is a distillate of blood serum and will therefore exhibit the same physiological characteristics as other body fluids, including osmolality.

Osmolality is a measure of the concentration of ions and particles in solution. It is fundamental to physiological processes as it affects diffusion of water molecules as, for example, across membranes. It is generally expressed as moles per kilogram of solvent or mmol. Normal blood serum or plasma has an osmolality of 285 to 295. Solutions of a higher osmolality are termed hypertonic solutions.

Until quite recently, the only devices capable of providing accurate measurements of osmolality required on the order of 1 to 2 ml of fluid, significantly more than can be obtained from the normal human joint. Recent technological advances, however, permit osmolality determinations, based on the dew point or freezing point depression, from samples of less than 20 microliters ($\mu l$).

Although it has been generally assumed that synovial fluid would exhibit an osmolality equivalent to that of blood serum, the technological improvements in measurement capability have resulted in the surprising observation that, under conditions of minimal activity, synovial fluid from normal subjects is, in fact, hypertonic in comparison to blood serum (Baumgarten et al., JBJS, in press, 1985). It thus appears that the osmolality of synovial fluid may be independently regulated by an ion pump which transports ions across the synovial membranes against an osmotic gradient, or some other mechanism of maintaining such a gradient. Strenuous exercise appears to induce a decrease in synovial fluid osmolality to the level of blood serum. Moreover, in certain pathological states, such as osteoarthritis and rheumatoid arthritis, the osmolality of synovial fluid is actually equal to or somewhat less than that of blood serum. Such lowered osmolality in the pathological state may, in fact, account in part for the swelling which occurs in the diseased or traumatized state by inappropriately facilitating the osmotic migration of fluid into the joint and surrounding tissues, including ligaments, tendons and nerve structures.

There thus exists the need for an irrigating solution which conforms to physiological parameters of normal synovial fluid for use in invasive medical procedures on the joints and soft tissues, particularly arthroscopic diagnosis and surgery. Additionally, there is a need for a solution which will reduce swelling of the synovial tissues, thereby decreasing or eliminating the synovitis associated with invasive arthroscopic procedures. The solution should be physiologically compatible in order to avoid injury to the tissues, and should be inexpensive and easily prepared. The present invention satisfies these needs and provides related advantages as well.

SUMMARY OF THE INVENTION

The present invention provides a physiologically conforming solution for use in invasive medical procedures such as surgical or other diagnostic or therapeutic treatment of the joints and soft tissues, which is hypertonic with respect to blood serum and may, in fact, have a higher osmolality than synovial fluid. The solution is of particular utility as an irrigant in arthroscopic surgery in order to reduce the risk of swelling and injury of the synovial tissues and as a therapeutic treatment for the swelling and subsequent inflammation of joints which occurs in certain traumatized and pathological states. The solution thus greatly reduces complications arising from invasive medical procedures. Further, it is inexpensive to make and easy to use.

In accordance with one aspect of the invention, there is provided an aqueous solution having therein certain ions, such as $Na+$, $Cl-$, $K+$ and $Ca++$, in amounts so as to conform to physiological standards. Moreover, the osmolality is regulated by the addition of sufficient protein, sugar, ions, metals or salts so as to render the solution hyperosmotic with respect to blood serum.

As an additional aspect of the invention, a method is provided for utilizing a hypertonic solution as an irrigant during an arthroscopic procedure on a joint. The use of a hypertonic solution reduces the risk of swelling and post-operative synovitis by effecting the osmotic regulation of fluid across the synovial membranes. In another aspect of the invention, the fluid can be used to reduce inflammation in synovial tissues which may result from certain pathological conditions such as osteoarthritis and rheumatoid arthritis, from sports or other trauma, and from post-surgical or intra-surgical inflammation.

The synovium in such traumatized and diseased joints is swollen due to inflammation. Cells and tissues in such a state produce and release inflammatory products which act as irritants to surrounding tissue, thereby perpetuating the inflammatory process. By infusing a hypertonic solution into the joints so as to bathe the tissues, an osmotic gradient is established which will tend to cause water and water soluble inflammatory products to be drawn out of the cells and tissues. This reduction of edema in turn decreases the production and release of inflammatory products, thereby checking the inflammatory cycle.

Other features and advantages of the present invention will become apparent from the following, more detailed description which illustrates, by way of example, the principles of the invention.

DETAILED DESCRIPTION OF THE PREFERRED EMBODIMENT

The present invention provides a physiologically conforming solution which is hypertonic with respect to blood serum for use in medical procedures involving joints and soft tissues, particularly arthroscopic procedures. The solution aids in the prevention of swelling and associated trauma resulting from the insult of arthroscopic surgery utilizing isotonic irrigants. Moreover, the solution aids in the treatment of swelling of the synovial cells and tissues, resulting from, for example, arthritis, sports trauma or operative procedures.

The solution comprises an aqueous solution having physiologically conforming concentrations of ions including, but not limited to, $Na+$, $K+$, $Cl-$ and $Ca++$. In a preferred embodiment, the solution comprises a modified lactated Ringer's solution (Travenol Laboratories, Deerfield, IL), in which the osmolality has been adjusted so as to be hypertonic, in the range of 350 to 450 mmols. Ideally, the osmolality is about 400 mmol. Preferably, mannitol, a five carbon alcohol, is added to achieve the desired osmolality. Mannitol is non-metabolizable and well-tolerated by the body and, because of its size, has strong osmotic effect. However, a range of substances including, but not limited to, proteins, ions, salts, metals or other electrolytes may also be used to regulate osmolality.

The composition of the preferred solution is as follows:

0.60% : Sodium chloride (NaCl)
0.31% : Sodium lactate (Na lactate)
0.03% : Potassium chloride (KCl)
0.02% : Calcium chloride ($CaCl_2$)

The pH is adjusted to about 7.3 by the addition of dibasic sodium phosphate ($Na_2HPO_4$) and the osmolality is adjusted to about 400 mmol by the addition of mannitol (approximately 26.69 g/l).

A hypertonic solution is advantageously utilized as an irrigant during arthroscopic procedures, particularly diagnostic and surgical procedures. A joint is entered via an ingress canula into the joint space. The joint is then distended by having two, 3-liter bags of the hyperosmotic physiologically balanced fluid suspended 1 meter and sometimes 2 meters above the patient. A second canula (egress) is placed within the joint to allow the constant flow of the hypertonic solution within the joint throughout the surgical procedure. The hypertonic solution provides the joint distention and also bathes the joint and washes away debris that is produced as a result of surgery. Use of the hypertonic solution results in a reduction of post-operative swelling of the synovial tissues, thereby minimizing the associated synovitis.

A hypertonic solution may also be advantageously utilized as a therapeutic agent to treat swelling of the synovial tissues resulting either from pathological conditions such as osteoarthritis, rheumatoid arthritis and sports trauma, or intra-operative or post-operative swelling. For treatment of these pathologic joints, an ingress canula is placed in the joint space and the hypertonic solution allowed to flow into the joint. A second canula (egress) is then placed in the joint to allow a constant flow of the hypertonic solution. The solution is allowed to circulate within the joint for 30-60 minutes. This procedure can be repeated as often as is necessary to relieve inflammation.

EXAMPLE I

DETERMINATION OF THE OSMOLALITY OF SYNOVIAL FLUID

Volunteers who were determined to be free of joint pathology by physical and radiographic examination were instructed to minimize their physical activity for one day. After being seated for one hour, each volunteer lay supine on an examination table with the hip flexed at about 45°, and the knee elevated at about 18° and flexed about 15°. Following skin anesthesia with 1% lidocaine, an 18 gauge needle was introduced into the suprapatellar pouch via the lateral aspect of the knee and fluid aspirated into a three milliliter syringe.

Synovial fluid was obtained from 13 of the 15 knees so aspirated, with two unsuccessful, dry taps. All aspirations were considered "atraumatic" by the visual absence of blood. Within 30 seconds of aspiration, an 8 μl sample of the synovial fluid was transferred via a Wescor micropipette having a precision sampling tip (Wescor Inc., Logan, UT) to a small paper sample disc (Wescor, Inc., Logan, UT), which was then inserted into the precalibrated Wescor 5100C vapor pressure osmometer (Wescor, Inc., Logan, UT). The osmolality was immediately determined. Blood samples were obtained from each volunteer concurrently with the synovial fluid. The blood was centrifuged in heparinized capillary tubes and the osmolality of the plasma determined with the Wescor 5100C. The mean synovial fluid osmolality of the 13 knees at rest was 404 mmol (SD±57). Blood plasma from volunteers at rest averaged 305 mmol (SD±10).

EXAMPLE II

CANINE EXPERIMENTAL MODEL

Greyhounds aged 2-3 years, weighing 55-70 lbs. and free of any obvious joint abnormalities, were used as experimental subjects Following xylazine/ketamine intravenous induction, the animal was intubated and placed on a methoxyflurane/oxygen gas mixture for maintainence of anesthesia. The dorsal aspects of both knee joints were prepared using standard sterile technique. An 18 gauge × 1.5 inch ingress needle was placed in the superior medial femorotibial pouch and the joint capsule distended using the test solutions ranging from 255 mmol to 725 mmol through a 35 ml syringe. With the joint capsule distended a second 18 gauge × 1.5 inch needle was placed in the inferior lateral femorotibial pouch to serve as an egress line to remove fluid from the joint. The test solution was dripped into the knee via a 3-liter bag suspended one meter above the knee at a rate of approximately one liter/hour. The test fluid circulated the joint, exited by the egress canula and was collected. After one hour (approximately one liter of solution) the ingress and egress needles were removed and the animal was sacrificed by barbiturate overdose. The test knee was immediately dissected by a medial parapatellar incision and the patella was released laterally. Synovium samples were carefully taken by sharp dissection at the medial and lateral femoromeniscal and tibiomeniscal joint sacs. Samples were also harvested from the superior, middle and inferior femoropatellar pouch. There was no test fluid circulated through the contralateral knee and the tissues harvested from it served as a control.

EXAMPLE III

ENZYME HISTOCHEMISTRY OF SYNOVIAL MEMBRANE

Following the principles of Reimann and Christensen (Clin. Orthop. and Related Research, 140:85-91, 1979) the enzyme activity within the synovial tissue of the control and those synovial tissues exposed to 250, 350, 400, 450, and 725 mmol fluids were examined to find which range of osmolality would be most physiologically compatible.

In order to determine the activity of acid phosphatase in the synovial tissue samples, the method of Barka and Anderson (*Histochemistry*, New York: Harper & Row, 1963) was used, as modified by Bancroft and Stevens (*Theory and Practice of Histological Techniques*, 2nd edition, Edinburgh: Livingstone, 1982), which is incorporated by reference.

After the experimental procedures described in Example II, synovium samples were carefully taken by sharp dissection at the medial and lateral femoromeniscal and tibiomeniscal joint sacs. Samples were also harvested from the superior, middle and femoropatellar pouch of the experimental and control knees. The tissues were snap frozen in isopentane in liquid nitrogen. Frozen sections were cut at 5 μm in a cryostat at −20° C. The sections were fixed with formalin vapor for 3 minutes, immediately immersed in a freshly-made solution composed of 10 ml 0.1 M acetate buffer pH 5.0, 10 mg sodium alpha naphthyl phosphate, and 10 mg Fast Garnet GBC, and incubated at 37° C. The sections were washed in distilled water and counterstained with 2% methyl green for approximately 5 minutes, washed in running tap water, and mounted in glycerin jelly. A positive reaction time was noted when red granules appeared under the microscope.

In order to obtain a measure of enzyme activity, the time from incubation to appearance of first color reaction was recorded. Observations were made with the Zeiss Photomicroscope III (Carl Zeiss, Inc., Thornwood, NY) at a magnification of 160x. A stop-watch was started immediately on immersing the frozen sections into the incubating media. Upon the recognition of red granules within the synovial tissue, the observation time was noted and plotted per FIG. 5. The results are presented in FIG. 5, closed triangles.

The activity of alkaline phosphatase in synovial membranes was determined according to Pearse's modification of Barka and Anderson (Pearse, A.G.E. *Histochemistry. Theoretical and Applied*, 3rd edition, Vol. 1. London: J and A. Churchill Ltd., 1968), which is incorporated by reference.

Frozen sections are prepared as for acid phosphatase. The sections were air dried and immersed in the incubating medium comprising 20 ml tris buffer pH 9.1, 20 mg sodium alpha naphthyl phosphate, and 20 mg Fast Red TR and incubated at room temperature. A positive reaction time was noted when brown granules appeared under the microscope.

The sections were washed in distilled water, then counterstained with nuclear fast red, rinsed in distilled water and mounted in glycerin jelly. Enzyme activity was measured as for acid phosphatase. Observations were made with the Zeiss Photomicroscope III (Carl Zeiss, Thornwood, NY) at a magnification of 160x. A stopwatch was started immediately on immersing the frozen sections into the incubating medium. Upon the recognition of brown granules within the synovial tissue, the observation time was noted and plotted as per FIG. 5, open circles.

The enzyme reaction time of the tissues treated with the test fluids was compared with the control tissue to provide a measure of the physiological compatibility of the test fluids. The tissues bathed in fluid having osmolality between 350-450 mmol were similar in enzyme reaction time to the enzyme reaction time of the normal control indicating the maintenance of normal metabolic cellular activity.

Tissues bathed in solutions at 250 and 725 mmol showed a marked difference in the enzyme activity when compared with the control synovium demonstrating a disturbance of the metabolic cellular activity. This observation correlates well with the ultrastructural changes detailed in Example IV. Additionally, the comparison of the proximity of the reaction times of alkaline phosphatase and acid phosphatase were similar in the control synovium and the synovium bathed with test fluid in the 350 to 450 mmol range, again attesting to the physiological compatibility of the fluid in this range.

Figure 5:
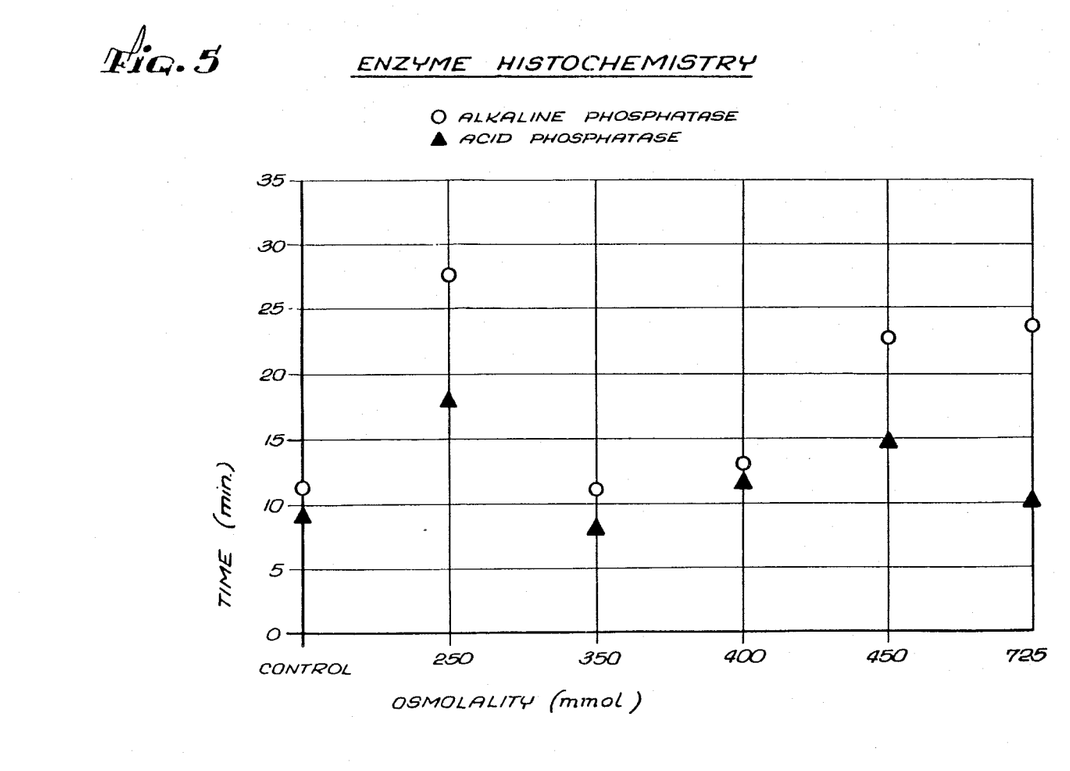
FIG. 5 is a graph showing the activity of alkaline phosphatase and acid phosphatase as a function of time in synovial tissues exposed to fluids of varying osmolalities and in an untreated control.

As can be observed in FIG. 5, there is a marked difference of reaction time between alkaline phosphatase and acid phosphatase at the 250 mmol and 725 mmol level, indicating a disturbance in the normal metabolic pattern. In general, the overall enzyme activity of the synovium bathed in fluids in the 350 to 450 mmol range was very similar to that of the control.

The significance of the enzyme reaction time attests to the physiological compatibility of the test fluid in the 350 to 450 mmol range.

EXAMPLE IV

ELECTRON MICROGRAPHIC HISTOLOGY OF SYNOVIAL MEMBRANES

After sacrifice of the animals exposed to the protocol of Example II, synovial samples were carefully taken by sharp dissection at the medial and lateral femoromeniscal and tibiomeniscal joint sacs. Samples were also harvested from the superior, middle and inferior femoropatellar pouch. The samples were cut into tiny cubes with a scalpel blade and fixed at once in cold cacodylate buffered 4% glutaraldehyde. The tissues were processed using a standard 24 hour processing technique for infiltration and embedded in Epon 812 (Medcast Resin) (Ted Pella, Inc., Tustin, CA). Specimens were stained with 4% uranyl acetate before embedding. Thick (0.5 $\mu$m) sections were cut on an ultramicrotome (Reichert Co., Buffalo, NY) using a diamond knife and stained with toluidine blue. Relevant areas (epithelial membrane and villus structures) were chosen and sections were further cut at 500–600 angstroms and mounted on grids. The grids were stained with lead citrate. Attention was focused on cell organelles (mitochondria, golgi apparatus, lysosomes, etc.) and both nuclear and cytoplasmic membranes assessed for continuity and integrity. As controls, normal tissue which had not been exposed to fluid treatment was prepared using an identical protocol. The synovial specimens from the control and synovium bathed in 250, 350, 400, 450 and 725 mmol test solutions were inserted into the JEOL 1200EX Electron Microscope (JEOL USA, Inc., Peabody, MA) for ultrastructural observations to assess the effects of the various osmotic stresses on the cell membrane, organelles and nucleus of the synovial cells.

The ultrastructure of the type A and B cells of the synovial tissue were photographed at identical magnifications to allow accurate assessment of the differences between the organelles and cell membranes of the tissues bathed in the various osmotic test fluids (250, 350, 400, 450 and 725 mmol). This allowed for accurate comparison with the control tissue. The specimens were photographed using Kodak 4489 film (Eastman Kodak Co., Rochester, NY).

Figure 1:
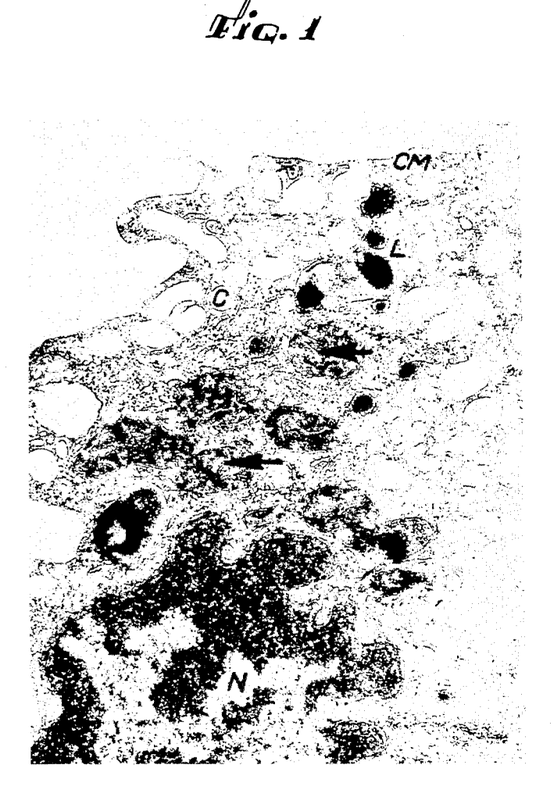
FIG. 1 is an electron micrograph of synovial tissue from the knee of a normal, untreated dog.

The control tissue, FIG. 1, showed good resolution of the nuclear (N) and cytoplasmic membranes (CM). Mitochondria (M) and golgi were well preserved in the Type A and Type B synovial cells. The cristae are well delineated (arrows) and show normal mitochondrial morphology. Vacuoles (C) are of normal size and have preserved integrity as do the lysosomes (L).

Figure 2:
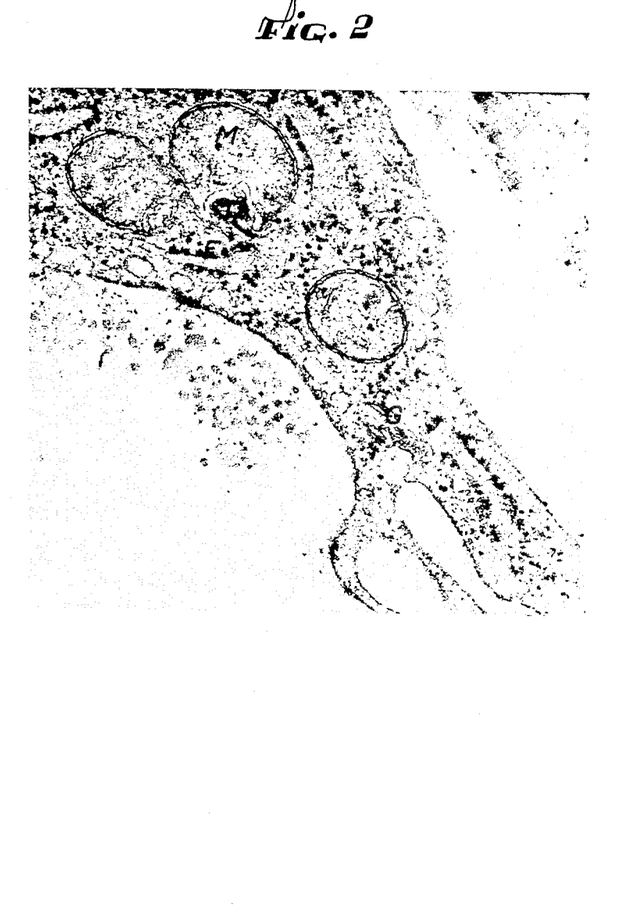
FIG. 2 is an electron micrograph of synovial tissue from the knee of a dog exposed to fluid having an osmolality of 250 mmol.
Figure 3:
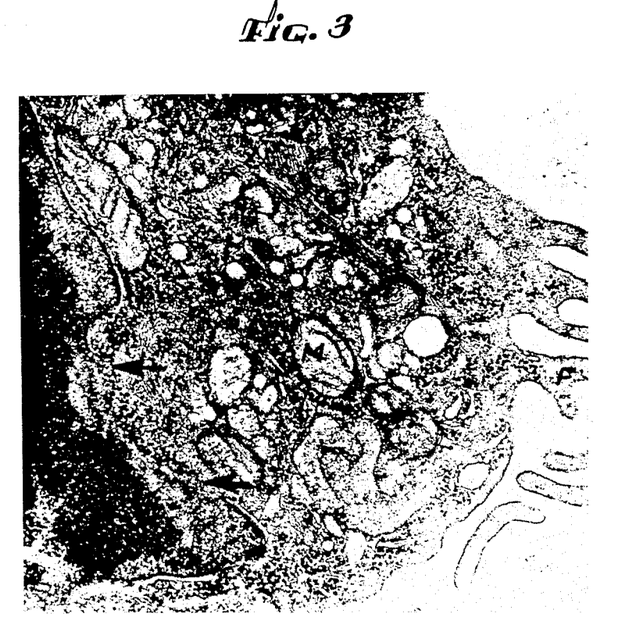
FIG. 3 is an electron micrograph of synovial tissue from the knee of a dog exposed to fluid having an osmolality of 725 mmol.

In contrast, FIG. 2 shows a type B cell with rough endoplasmic reticulum (E) and 3 altered mitochondria (M) resulting from the exposure to the 250 mmol test solution. The mitochondria are swollen and show shortening and loss of cristae. A degenerative particle (D) resulting from the osmotic stress, can be observed in the mitochondria. An atrophic Golgi apparatus (G) is seen without vesicles or vacuoles which is another ultrastructural change which can be attributed to the 250 mmol osmotic stress. FIG. 3 shows a cell with dilated cisternae and swollen mitochondria (M) with loss of cristae resulting from the extremely hyperosmotic stresses exerted by the 725 mmol fluid. Other features indicative of cell damage from this non-physiologically conforming fluid are elongated filopodia (F) and loss of nuclear membrane integrity (arrows).

Figure 4:
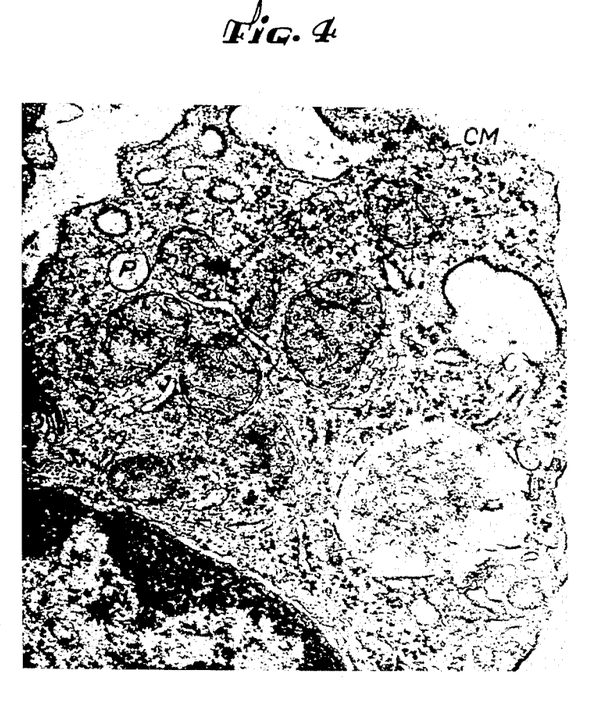
FIG. 4 is an electron micrograph of synovial tissue from the knee of a dog exposed to fluid having an osmolality of 400 mmol.

FIG. 4 shows a type A cell bathed in 400 mmol test solution, pinocytotic vesicles and vacuoles (P) that appear normal and similar to those of the control tissues. The nuclear (N) and cytoplasmic membranes (CM) are seen to be structurally similar to those of the control tissue. The smooth walled vesicles and well preserved mitochondria (M) with characteristic irregular cristae (arrow) again parallel the ultrastructural features present in the control tissue. The cellular ultrastructure seen in FIG. 4 is typical for synovium bathed in 350–450 mmol test solutions.

The synovium from animals treated with the 250 mmol and 725 mmol solutions demonstrate ultrastructural damage indicative of the non-physiologically conforming nature of the solutions. In contrast, synovium bathed with 400 mmol test solution showed ultrastructure comparable to that of the control, demonstrating the physiological compatibility of this fluid.

EXAMPLE V

TREATMENT OF TRAUMATIZED JOINTS

For treatment of pathologic joints exhibiting inflammation and swelling, an ingress canula is placed in the joint space and the hypertonic solution allowed to flow into the joint. An egress canula is then placed in the joint to allow a constant flow of the hypertonic solution. The solution is allowed to circulate within the joint for 30–60 minutes. This procedure can be repeated as often as is necessary to relieve inflamation.

Although the invention has been described with reference to the presently-preferred embodiment, it should be understood that various modifications can be made by those skilled in the art without departing from the invention. Accordingly, the invention is limited only by the following claims.

What is claimed is:

1. A composition for use in invasive medical procedures, comprising:
   a solution containing ions selected from the group consisting of Na+, K+, Cl− and Ca++ having a hypertonic osmolality between about 350 mmol to about 450 mmol relative to the osmolality of normal mammalian blood serum and conforming to the ionic composition of normal mammalian synovial fluid so as to be physiologically compatible with joints and tissues during said medical procedures.

2. A method of treating the condition of swelling of the synovial cells and tissues of a joint, and for reducing intra- and post-operative inflammation of the tissues proximate to the area of an invasive medical procedure comprising the steps of:
   providing a solution having a hypertonic osmolality relative to the osmolality of normal mammalian blood serum and conforming to the ionic composition of normal mammalian synovial fluid so as to be physiologically compatible with said cells and tissues;

bathing said synovial cells and tissues of a joint with said solution; and removing said solution from said synovial cells and tissues.

3. The method of claim 2, wherein said synovial cells and tissues are bathed by placing an ingress canula and an egress canula in said joint and providing a flow of said solution therethrough.

4. The method of claim 2, wherein said hypertonic osmolality is in the range of about 350 mmol to 450 mmol.

5. The composition of claim 1 wherein the osmolality of said solution is adjusted with mannitol.

6. The composition of claim 1 wherein the osmolality of said solution is about 400 mmol.

7. The composition of claim 1 wherein the solution is lactated Ringer's solution altered to have an osmolality of between about 350 mmol to about 450 mmol.

8. The method of claim 2 wherein the step of providing a solution having a hypertonic osmolality further comprises providing a solution having an osmolality between about 350 mmol to about 450 mmol.

9. The method of claim 2 wherein the step of providing a solution having a hypertonic osmolality further comprises providing a solution containing ions selected from the group consisting of $Na^+$, $K^+$, $Cl^-$ and $Ca^{++}$.

* * * * *

UNITED STATES PATENT AND TRADEMARK OFFICE
CERTIFICATE OF CORRECTION

PATENT NO. : 4,872,865

DATED : October 10, 1989

INVENTOR(S) : Roy D. Bloebaum, Frank P. Magee

It is certified that error appears in the above-identified patent and that said Letters Patent is hereby corrected as shown below:

In the claims, column 10, line 15, insert claim 10:

> 10. The composition of claim 1 wherein said solution contains 0.60% sodium chloride, 0.31% sodium lactate, 0.03% potassium chloride and 0.02% calcium chloride.

Signed and Sealed this

Eighteenth Day of September, 1990

Attest:

*Attesting Officer*

HARRY F. MANBECK, JR.

*Commissioner of Patents and Trademarks*